United States Patent [19]

Fyodorov et al.

[11] Patent Number: 5,093,125
[45] Date of Patent: Mar. 3, 1992

[54] OPHTHALMOLOGICAL COLLAGEN COVERINGS

[75] Inventors: Svyatoslav N. Fyodorov; Sergey N. Bagrov; Tatyana S. Amstislavskaya; Irina A. Maklakova; Sergey V. Maslenkov, all of Moscow, U.S.S.R.

[73] Assignee: Moskovsky Nauchno-Teknichesky Compleks "Mikrochirurgija Glaza", Moscow, U.S.S.R.

[21] Appl. No.: 587,576

[22] Filed: Sep. 21, 1990

Related U.S. Application Data

[60] Continuation of Ser. No. 461,167, Jan. 5, 1990, abandoned, which is a division of Ser. No. 131,958, Dec. 11, 1987, Pat. No. 4,913,904.

[51] Int. Cl.$^5$ .............................................. A61F 2/14
[52] U.S. Cl. ................................... 424/427; 424/428; 424/429; 530/356; 623/4; 514/912; 514/955; 602/50
[58] Field of Search ............ 424/427, 428, 429; 530/356, 357; 435/273; 523/105, 106; 128/76.5, DIG. 8; 623/4, 5; 264/1.7, 2.6, 2.7

[56] References Cited

U.S. PATENT DOCUMENTS

| | | | |
|---|---|---|---|
| 3,553,299 | 1/1971 | Thiele et al. | 264/1.7 |
| 3,637,642 | 1/1972 | Fujii | 530/355 |

OTHER PUBLICATIONS

Stryer, *Biochemistry*, 2nd Ed., W. H. Freeman and Co. 1981, pp. 18-19.

*Primary Examiner*—Thurman K. Page
*Assistant Examiner*—Amy Hulina
*Attorney, Agent, or Firm*—Burgess, Ryan and Wayne

[57] ABSTRACT

Ophthalmologic collagen coverings derived from animal eyes and a process for preparing such coverings comprising treatment of a fibrous tunic of an animal eye with an alkali metal hydroxide in a saturated solution of a salt of an alkali metal, followed by neutralization, dissolution in an aqueous solution of an organic acid, purification of the resulting solution of collagen by dialysis against a buffer solution while bringing the solution of collagen to a pH of 4.5 to 7.5 and drying the thus-obtained solution of collagen simultaneously with shaping spherical coverings therefrom.

1 Claim, No Drawings

OPHTHALMOLOGICAL COLLAGEN COVERINGS

This application is a continuation of Ser. No. 07/461,167 filed Feb. 5, 1990, now abandoned, which is a division of Ser. No. 07/131,958 now U.S. Pat. No. 4,913,904.

BACKGROUND OF THE INVENTION

This invention relates to a form of collagen that is uniquely suited for ophthalmic uses. In more specific embodiments, this invention relates to a process for preparing ophthalmological collagen coverings and to coverings prepared by this process and useful in all kinds of ophthalmological operations, as well as in a conservative treatment of traumatic and trophic injuries of the cornea of the eye having different etiology.

The present stage of the development of eye surgery features a high quality of surgical treatment. In this respect there is a problem of developing new methods and agents making it possible to reduce the number of post-operational complications, to shorten the time of hospital stays, and to ensure higher functional results of operations on the globe of the eye.

Known in the art are materials produced from collagen and methods of dissolution of collagen derived from the skin and tendons of animals. Thus, a known process for dissolution of collagen of an animal skin (USSR Inventor's Certificate No. 162280, 1964) comprises an alkali-salt treatment of an animal skin with a subsequent neutralization and residence in an acidic medium to give a dispersion of collagen having pH of not higher than 2.5.

Known in the art is a process for preparing a hemostatic material from a dispersion of collagen (cg. USSR Inventor's Certificate No. 561564, 1977). Acidification of neutral dispersions of collagen obtained after an intensive alkali-salt treatment of animal skin and tendons are intermixed with thrombin and antibiotics, whereafter the mixture is frozen and dried in vacuum.

These processes cannot be employed for the preparation of collagen coverings to be used in ophthalmology, since the materials produced by these processes have clearly pronounced antigenic properties.

It is an object of the present invention to provide a process for preparing and using ophthalmological collagen coverings. A particular object, is a covering for use in connection with microsurgical operations on the globe of the eye. A further object is an improved conservative treatment of traumatic and trophic injuries of the cornea of the eye having different etiology. Other objects will be apparent from consideration of the following description of the invention.

SUMMARY OF THE INVENTION

It has been found that collagen isolated from animal eyes, especially the fibrous tumic of animal eyes and preferably the sclera of animal eyes, is specially suited for topical application to the eye, avoiding antigenic characteristics associated with collagen derived from, e.g., animal dermis. The collagen also possesses therapeutic properties making it desirable for the treatment of traumatic and trophic injuries of the cornea. The collagen further possesses lubricating properties suggesting the potential for the treatment of dry eye.

The collagen may be provided in a variety of forms adapted for ophthalmic use. Examples include membranes, gels, and solutions. Especially preferred for the treatment of traumatic and trophic injuries are shaped collagen articles (described in more detail below). Collagen applied to the eye in the form of, e.g., drops or ointments is washed relatively rapidly from the eye by tear flow. By contrast, collagen applied as a shaped article is maintained in the eye for a longer periods, extending the desirable therapeutic effects of the application. Even when applied as a shaped article, however, the collagen is bioerodible and will dissolve in the eye.

The preferred process for isolating collagen from animal eyes and for preparing ophthalmological collagen coverings comprises treating the fibrous tunic of an animal eye with an alkali metal hydroxide in a saturated solution of an alkali metal salt, then neutralizing the resulting tissue to a pH from 6.0 to 7.0, and dissolving the tissue in an aqueous solution of an organic acid; the thus-prepared solution of collagen is decontaminated from low-molecular impurities by dialysis against a buffer solution while bringing pH of the solution of collagen to 4.5–7.5 and the obtained solution of collagen is dried simultaneously with shaping therefrom spherical coverings repeating the curvature of the front section of the eye.

With the view to improve quality of the resulting covering, as the starting material—fibrous tunic of an animal eye use is preferably made of the sclera of animal eyes.

The neutralization of the tissue should be preferably effected by means of a 2% solution of boric acid. For dissolution of collagen any organic acid can be used, acetic acid being preferable. The ophthalmological collagen coverings prepared by the process according to the present invention has a spherical shape repeating the curvature of the front section of the eye and ensuring a full contact with the surface of the cornea of the eye; they also have dimensions ensuring a full coating of the cornea.

The ophthalmological collagen coverings according to the present invention are applied onto the front surface of the cornea and serve as a temporary hydrophilic spherical "bandage" and kept on the front surface of the cornea without any additional fixation while exhibiting therapeutical properties of a naturally-occuring copolymer—collagen.

The coverings according to the present invention make it possible to reduce the number of post-operational complications, accelerate healing of injured tissues of the eye. In the case of traumatic and trophic injuries of the cornea the collagen coverings according to the present invention enable normalization of metabolic processes in the injured cornea. The coverings of this invention are useful in the front radial keratotomy, especially in the case of appearance of microperforations, in keratoplasty, keratoprosthetics, in the treatment of post-operational keratopathy, endothelial-epithelial dystrophy, erosion of the cornea. The use of ophthalmological collagen coverings makes it possible to reduce the number of post-operational complications, in 98% of cases there has been noted the formation of more soft cicatrices on the cornea after keratotomy; in 98% of cases there has taken place a lesser degree of edema of the cornea and the transplantate edema in keratoplasty. In trophic injuries of the cornea having different etiology positive dynamics has been noticed in 95% of cases as compared to previously carried out conservative therapy with the use of pharmaceutical preparations.

DETAILED DESCRIPTION OF THE INVENTION

The source of the collagen is mammalian eyes, preferably the eyes of animals, and most preferably agricultural animals, such as pigs. The collagen may be extracted from any collagen containing, discrete portion of the eye or from the whole intact eye, but the preferred source of collagen is from the sclera of the eye. Collagen isolated from animal eyes and used in ophthalmological products according to this invention causes minimal allergic reaction and less eye inflammation as compared to collagen isolated from other sources, such as bovine hide.

The fibrous tunic of an animal eye is thoroughly cleaned from internal coats of the eye, residual epithelium, conjunctiva, muscles and miscellaneous; and stroma is isolated.

The isolated stroma is cut into small pieces. The cut tissue is rinsed with distilled water to completely remove mechanical foreign matter and blood, then it is transferred into a flask to which is then added an alkali metal hydroxide in a saturated solution of a salt of an alkali metal, for example, with a 10% solution of caustic soda in a saturated solution of sodium sulphate (at a rate of 500 ml of the solution per 10 g of the tissue) for 48 hours at a temperature of 18°-25° C. The solution is decanted and the tissues are subjected to neutralization to a pH of 6.0-7.0 under stirring, e.g. in a 2% solution of boric acid and repeatedly changing the solution. The tissue is rinsed with distilled water until a complete removal of the sulphate ion in the rinsing liquid The rinsed tissue is then dissolved in a 0.5-1M solution of an organic acid such as acetic acid in such quality that the final concentration of protein in the solution be equal to 1%. As the organic acid use can be made of citric acid, lactic acid, ascorbic acid and the like. The mass is stirred and allowed to stand in a refrigerator for 1-3 days at a low temperature. Then the mass is homogenized, centrifuged and allowed to stand for one day at a low temperature. The resulting solution is filtered. To carry out neutralization and desolvation, the acetic-acid solution of collagen is diluted with acetic acid to a concentration of protein of 0.7-0.8% and dialyzed against a phosphate or citrate buffer at a temperature of 18°-20° C. while bringing pH of the solution of collagen to 4.5-7.5. The resulting collagen solution is centrifuged, poured into matrices repeating the shape of the front section of the eye and air-dried in a dust-free cabinet at a temperature within the range of from 10° to 27° C. Ophthalmological collagen coverings are thus obtained which are elastic, transparent, or a spherical shape repeating the curvature of the front section of the eye. The size and shape of coverings ensure a full coating of the cornea of the eye and its full contact with the front surface thereof. The final coverings are sterilized.

Preferred embodiments of the foregoing process steps are:

1. The sclera pieces are treated with an aqueous solution comprising from 1.0 to 3.0 molar alkali metal hydroxide and from 0.8 to 1.5 molar alkali metal sulfate, preferably 2.5 molar sodium hydroxide and 1.4 molar sodium sulfate having a pH of about 12-14. Sclera is treated with stirring for about one to three days, preferably for two days. The weight to volume ratio of sclera to treatment solution is from about 15 to 25 rams per liter, preferably about 20 grams per liter.

2. The sclera is neutralized to a pH of about 6 to 7 by draining the hydroxide solution and treating first with distilled water and then with a dilute aqueous acid solution having a pH of about 3-5, preferably 4 to 4.5. Acids useful for neutralization include boric acid, tararic acid, citric acid, acetic acid, lactic acid and ascorbic acid. Boric acid is preferred for neutralization, with a concentration of about 0.02 to 0.04 molar, preferably 0.030 to 0.033 molar. Treatment cycles are typically 15 mintues to two hours, with constant stirring. The weight to volume ratio is typically 20 grams (initial starting weight) to from about 500 milliliters to one liter treatment solution. Two to five acid treatments are used to neutralize the sclera; preferably, three treatments are used. The sclera is rinsed with distilled water following neutralization; preferably, three times for about 1 hour each rinse.

3. The sclera is then dissolved in an aqueous organic acid solution to a concentration of about 0.5% to 1.5% by weight collagen, preferably to a concentration of 1%. Acids suitable for preparation of collagen solution are the organic ones listed previously for neutralization of sclera. The collagen is dissolved by incubation in a suitable aqueous organic acid, preferably acetic acid, with a concentration of about 0.1 to 2 molar, preferably 1 molar, with stirring for about two to four days, preferably three days, at a temperature of about 2 to 10 degrees centigrade, preferably 4 to 6 degrees centigrade.

4. The collagen solution is conveniently homogenized in a blender, centrifuged and filtered. The collagen solution is then dialyzed against an aqueous buffer, see e.g. U.S. Pharmacopeia XXI, 1985, page 1420, such as phosphate or citrate, preferably citrate, having a concentration of about 0.002 to 0.2 molar, and a pH of about 7.0 to 8.0, preferably 7.2. Dialysis is continued with addition of fresh citrate buffer until the pH of the collagen is from about 4.5 to 7.5, preferably about 5.0 to 5.5, the collagen solution has formed a cloudy, homogenous ge. Dialysis may be accomplished by various techniques known to the art. Typically, dialysis membranes are used having molecular weight cut-off limits of from about 3,000 to 100,000, preferably from about 10,000 to 100,000. These membranes easily retain the extracted collagen, which has an average molecular weight of about 300,000. This molecular weight is typical of tropocollagen, defined herein and in the literature as the basic molecular subunit of collagen, existing as a rigid rod consisting of three polypeptide chains wound together in a triple helix.

5. The collagen gel is conveniently homogenized in a blender, centrifuged, deaerated, and filtered to remove particulate matter from the gel.

The collagen of this invention can be used as a vehicle for drug delivery. For example, shaped collagen may be impregnated with an ophthalmically active drug or collagen solution or gels may be employed to produce soluble preparations for ophthalmic use. Selection of the ophthalmically active drug is not critical to this invention, although materials such as pilocarpine, dexamethazone, and gentamycin may be mentioned as being exemplary.

Shaped collagen articles prepared as described above have very little cross-linking, and, consequently, dissolve in a relatively slow period of time. Dissolution rate of the collagen may be slowed if desired by introducing a minor amount of cross-linking into the collagen structure. This may be accomplished by any of the techniques well-known in the art. Radiation induced cross-linking is particularly convenient. However, the degree of cross-linking, if induced is limited to that which does not undermine the bioerodible properties of the articles.

The process according to the present invention makes it possible to prepare ophthalmological collagen coverings the use of which contributes to reducing post-operational complications, accelerates healing of injured tissues of the eye, reduces hospital stays of post-operational treatment of patients. The use of coverings according to the present invention in the case of traumatic and trophic injuries of the cornea exerts a favorable influence on metabolic processes in the cornea which is objectively revealed in diminished photophobia, lachrymation, edema of the cornea, better acuity of vision. This invention, and properties of the products, will be better understood by reference to the following examples.

EXAMPLE 1

To 20 g of purified and cut stroma of sclera of an animal eye 1 liter of a 10% solution of caustic soda in a saturated solution of sodium sulphate is added and allowed to stand at a temperature of 18°-20° C. for 48 hours. Then the solution is decanted, the tissue is rinsed with a small amount of distilled water, added with 1 liter of a 2% solution of boric acid and agitated by means of a magnetic stirrer for 2 hours twice changing the solution of boric acid. Under continuous stirring the tissue is thoroughly rinsed with distilled water (total volume of water—5 liters) till a complete removal of the sulphate ion from the rinsing liquid. 250 ml of the resulting water-treated tissue are added with 350 ml of a 0.5M acetic acid, stirred and left for one day at the temperature of 4° C. Then the mass is homogenized by means of a microdisintegrator of tissues, centrifuged for 30 minutes at 2,000 r.p.m. and allowed to stand for 3 days at the temperature of 4° C. The resulting solution is filtered through a glass filter. The thus obtained 1% solution of collagen is diluted with a 0.5M solution of acetic acid to the concentration of 0.8%. The dialysis of the 0.8% solution of collagen is effected against a 0.2M citrate buffer while bringing pH of the solution of collagen to 6.7. The dialysis is continued while lowering the buffer concentration from 0.2M to 0.002M in 3-4 stages using, in the last stage, heating to a temperature of 28°-30° C. The resulting solution of collagen is centrifuged for 15 minutes at 1,000 r.p.m., poured into matrices repeating the shape of the front section of the eye and air-dried in a dust-protected cabinet for 48 hours at the temperature of 15° C. and relative humidity of 40-50%. The final coverings are sterilized by gamma-rays in the dose of 2.5MRad and dose rate of 0.5MRad/h.

The thus-prepared coverings are transparent, elastic; they have a spherical shape repeating the curvature of the front section of the eye. The shape and dimensions ensure a full coating of the cornea of the eye and a full contact with the front surface thereof.

EXAMPLE 2

Twenty grams of comminuted sclera, derived from porcine eyes, were treated in a one liter flask with 980 milliliters of a solution comprised of 100 grams per liter sodium hydroxide and 200 grams per liter sodium sulfate in distilled water by stirring continuously for 48 ours. The solution was then drained and the sclera rinsed by a 5 minute stirring cycle with 1 liter of distilled water. The sclera was then neutralized by three 1 hour stirring cycles, each in one liter of a solution comprised of 20 grams boric acid per liter in distilled water, followed by two 15-minute stirring cycles, each in one liter of distilled water. During neutralization, the sclera swells significantly and becomes soft and transparent. The swollen sclera was then dissolved in 530 milliliters of 1 molar acetic acid by stirring at 4 degrees centigrade for 48 hours to form a collagen solution having an approximate concentration of 1%. The resulting collagen solution was homogenized in a blender, centrifuged to remove air bubbles and filtered to remove fine retinal fragments. The collagen solution was then placed in dialysis tubing having a molecular weight cut-off of 10,000-12,000 and dialyzed against 25 liters of a citrate buffer solution comprised of 22.5 grams of sodium citrate in 25 liters of distilled water, pH adjusted to 7.2 with 1 molar hydrochloric acid. As a result of the dialysis, the collagen solution formed a cloudy, white, homogeneous gel and had a pH of 5.2. The gel was then homogenized in a blender, centrifuged, deaerated and filtered.

The resulting solution was cast into molds conforming to the curvature of the eye and allowed to dry at room temperature in a laminar flow hood for 72 hours. The corneal coverings have an average thickness of about 0.002 inches and weigh about 0.003 grams.

COMPARATIVE EXAMPLE A

Dialysis is a critical step in the production of collagen material suitable for casting. When cast from acidic, predialysis solutions, the resulting collagen coverings are typically malformed with numerous inhomogeneities and defects. Because of differences in the vapor pressures of water and acetic acid, and in solutions employing other acids, acid concentration can increase upon drying causing denaturation of the collagen. As an example, collagen derived as described in Example 1 but only dialyzed against 10 liters of buffer, has a pH of 3.5 and will not cast clear, homogeneous films, free of imperfections.

EXAMPLE 3

The significance of the use of the collagen covering disclosed herein following ophthalmic surgery of corneal trauma has been demonstrated in experiments in rabbits. Rabbits were subjected to standard radial keratotomy procedures in both eyes, and one eye was covered with a collagen covering immediately following surgery. Examination at various times following surgery showed a marked decrease in traumatic inflammation and edema at all time following surgery for the eyes treated with the coverings. It was also observed that incisions without the covering windened as they healed, filling with a wedge of epithelium while those treated with collagen covering were held together and "bridged" by the covering. Fibroblast proliferation at the site was two to three times greater than the controls indicating higher levels of collagen synthesis. The coverings dissolved within two to six hours.

It has also been found that if collagen other than that derived from the eye, such as bovine dermal collagen, is used to cover ophthalmic wounds, inflammation and edema are more severe than for porcine eye collagen. Further, collagen from the eyes of pigs elicits somewhat less inflammatory response than from the eyes of cows.

The advantages of this invention will be apparent to those skilled in the art. Greatly improved, virtually non-allergic products are economically made available for the healing arts.

It will be understood that this invention is not limited to the specific examples which have been offered as particular embodiments, and that modifications can be made without departing from the spirit thereof.

What is claimed:

1. A method for isolating collagen from animal eyes which comprises:

(a). treating the sclera of an animal eye with an alkali metal hydroxide in a saturated solution of an alkali metal salt,
(b). neutralizing the resulting collagen tissue to a pH of 6.0–7.0,
(c). dissolving the collagen tissue in an aqueous solution of an organic acid, and
(d). dialyzing the resulting collagen solution against a buffer solution to raise the pH of the collagen to 4.5–7.5

* * * * *